US012715898B2

(12) United States Patent
Jiang et al.

(10) Patent No.: US 12,715,898 B2
(45) **Date of Patent: *Aug. 25, 2026**

(54) MOLECULAR PEPTIDE MUTANT

(71) Applicant: NANJING TECH UNIVERSITY, Nanjing (CN)

(72) Inventors: Ling Jiang, Nanjing (CN); Yao Chen, Nanjing (CN); Liying Zhu, Nanjing (CN); Wei Liu, Nanjing (CN); Xianhan Chen, Nanjing (CN); Xinyi Chen, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 433 days.

This patent is subject to a terminal disclaimer.

(21) Appl. No.: 18/255,108

(22) PCT Filed: Apr. 25, 2022

(86) PCT No.: PCT/CN2022/088907

§ 371 (c)(1),
(2) Date: May 31, 2023

(87) PCT Pub. No.: WO2022/237510

PCT Pub. Date: Nov. 17, 2022

(65) Prior Publication Data

US 2024/0002454 A1 Jan. 4, 2024

(30) Foreign Application Priority Data

May 12, 2021 (CN) ......................... 202110516304.3

(51) Int. Cl.
*C07K 14/315* (2006.01)
*C12N 15/70* (2006.01)

(52) U.S. Cl.
CPC ............ *C07K 14/315* (2013.01); *C12N 15/70* (2013.01)

(58) Field of Classification Search
None
See application file for complete search history.

(56) References Cited

U.S. PATENT DOCUMENTS 4,784,948 A * 11/1988 Scott ...................... C12N 15/70 435/480
2019/0389925 A1 12/2019 Powell et al.
2022/0040273 A1* 2/2022 Hou ...................... C07K 14/45
2024/0002454 A1* 1/2024 Jiang ...................... C12N 15/70
2024/0376160 A1* 11/2024 Jiang .................... C07K 14/245

FOREIGN PATENT DOCUMENTS

CN 105061581 A 11/2015
CN 112062856 A 12/2020
CN 113214369 A 8/2021
CN 114632148 B * 8/2024 ............. A61K 39/00

OTHER PUBLICATIONS

Liu, Yajie et al. “Tuning SpyTag—SpyCatcher mutant pairs toward orthogonal reactivity encryption”, Chemical Science, vol. 9, No. 8, Jul. 19, 2017, abstract, pp. 6577-6579.

* cited by examiner

*Primary Examiner* — Hope A Robinson
(74) *Attorney, Agent, or Firm* — PROI Intellectual Property US

(57) ABSTRACT

The invention relates to a molecular peptide mutant, the amino acid sequence of which is as shown in SEQ ID NO: 1. In the invention, SpyCatcher is designed and modified to obtain a molecular peptide SpyCatcher-21 with stimulus response to pH on the basis of not affecting the formation of isopeptide bonds, and Pro is introduced into a key loop of the SpyCatcher-21 through analysis of the crystal structure to reduce the flexibility of the loop and obtain a mutant SpyCatcher-21_A82P, which can raise ligation efficiency with SpyTag. The SpyCatcher-21_A82P can be used to achieve double-enzyme catalysis according to objective needs by changing the pH of the environment to obtain different degrees of coupling, or obtain a three-enzyme coupled catalytic system through electrostatic interaction with a positively charged enzyme.

1 Claim, 4 Drawing Sheets

Specification includes a Sequence Listing.

```
SpyCatcher-21        AMVDTLSGLSSEQGQDGDMTIEEDSATHIEFSKRDEDGKELAGATMELRDSSG
SpyCatcher-21_A82P   AMVDTLSGLSSEQGQDGDMTIEEDSATHIEFSKRDEDGKELAGATMELRDSSG
                                                   82
SpyCatcher-21        KTISTWISDGDVKDFYLYPGEYTFVETEAPDGYEVDDAITFTVNEDGQVTEEG
SpyCatcher-21_A82P   KTISTWISDGDVKDFYLYPGEYTFVETEPPDGYEVDDAITFTVNEDGQVTEEG

SpyCatcher-21        KATKGDAHI
SpyCatcher-21_A82P   KATKGDAHI
```

FIG. 1

```
                         SEQUENCE LISTING


<160> NUMBER OF SEQ ID NOS: 1

<210> SEQ ID NO 1
<211> LENGTH: 115
<212> TYPE: PRT
<213> ORGANISM: Artificial Sequence
<220> FEATURE:
```

-continued

```
<223> OTHER INFORMATION: Sequence is synthesized

<400> SEQUENCE: 1

Ala Met Val Asp Thr Leu Ser Gly Leu Ser Ser Glu Gln Gly Gln Ser
1               5                   10                  15

Asp Asp Met Thr Ile Glu Glu Asp Ser Ala Thr His Ile Glu Phe Ser
            20                  25                  30

Lys Arg Asp Glu Asp Gly Lys Glu Leu Ala Gly Ala Thr Met Glu Leu
        35                  40                  45

Arg Asp Ser Ser Gly Lys Thr Ile Ser Thr Trp Ile Ser Asp Gly Asp
    50                  55                  60

Val Lys Asp Phe Tyr Leu Tyr Pro Gly Glu Tyr Thr Phe Val Glu Thr
65                  70                  75                  80

Glu Pro Pro Asp Gly Tyr Glu Val Asp Asp Ala Ile Thr Phe Thr Val
                85                  90                  95

Asn Glu Asp Gly Gln Val Thr Glu Glu Gly Lys Ala Thr Lys Gly Asp
            100                 105                 110

Ala His Ile
        115
```

MOLECULAR PEPTIDE MUTANT

TECHNICAL FIELD

The present invention pertains to the field of design of a molecular peptide SpyCatcher and particularly relates to a molecular peptide mutant.

BACKGROUND ART

In 2010, the Mark Howarth team from the Biochemical Center, the University UK successfully isolated multiple polypeptide fragments that can spontaneously form isopeptide bonds from pilin of gram-positive bacteria *Streptococcus pyogenes*. These fragments were named SpyTag (13 amino acids) and SpyCatcher (116 amino acids), and Asp117 of the SpyTag can spontaneously form an isopeptide bond with Lys31 of the SpyCatcher. The SpyTag/SpyCatcher has been widely used in various fields, including protein purification, protein display systems, and so on. However, the original molecular peptide SpyTag/SpyCatcher has a wide range of reaction conditions and lacksa stimulus response behavior to the external environment. The changes in the charge density on the protein surface can alter many properties of the enzyme, including aggregation resistance, cell permeability, stimulus response behavior, and the ability to bind to oppositely charged macromolecules. However, it is important to note that amino acid mutations can be risky and may lead to inactivation of protein. Any modification made to the SpyCatcher may affect the ability of the system to form an isopeptide bond with SpyTag or alter its ligation efficiency.

SUMMARY OF THE INVENTION

An objective of the present invention is to provide a molecular peptide mutant, obtain a molecular peptide SpyCatcher-21 with stimulus response to pH on the basis of not affecting the formation of isopeptide bonds, introduce Pro into a key loop of the SpyCatcher-21 through analysis of the crystal structure to reduce the flexibility of the loop and obtain a mutant SpyCatcher-21_A82P, which improves the ligation efficiencies of the SpyCatcher-21 and the SpyTag on the basis of not affecting their surface potentials.

In order to achieve the foregoing technical objective, the present invention adopts the following technical solution:

A molecular peptide mutant, wherein the amino acid sequence is as shown in SEQ ID NO: 1.

Another objective of the present invention is to protect a gene sequence encoding the molecular peptide according to claim 1.

Another objective of the present invention is to provide an application of the foregoing molecular peptide in a double-enzyme or three-enzyme catalytic system.

Specifically, achieve double-enzyme catalysis by changing the pH of the environment to obtain different degrees of coupling of SpyCatcher-21_A82P and SpyTag; or obtain a three-enzyme coupled catalytic system through electrostatic interaction with a positively charged enzyme.

The molecular peptide in the present invention can be purified by the following method, comprising the following steps:

(1) introducing the gene sequence of the molecular peptide into a vector to construct a recombinant plasmid, and introducing the recombinant plasmid into a host bacterium;

(2) culturing the host bacterium containing the recombinant plasmid till $OD_{600}$=0.6-0.8, and then adding IPTG for induction;

(3) taking and centrifuging a bacteria solution after the end of the induction, collecting cells, adding a phosphate buffer solution for resuspension, and carrying out ultrasonication; and;

(4) carrying out ultracentrifugation of the crushed liquid, taking the supernatant, and carrying out purification dialysis to obtain purified protein.

Further, in the (1), the vector is pET-22b; the restriction enzyme sites ligated to the vector are Nde I and Xho I.

Further, in the (1), the host bacterium is *E. coli* BL21 (DE3).

Further, in the (2), *E. coli* (DE3) containing the recombinant plasmid is cultured in an LB medium.

Further, in the (4), the supernatant is subjected to protein purification in Ni-NTA resin.

Further, the purified protein is dialyzed in a 3,000 Da dialysis bag for 24-26 h.

The principle of mutant modification of the present invention is as follows: Through the analysis of the crystal structure (PDB ID 4 mli) of the SpyTag/Spycatcher, it is discovered that Tyr119 and Lys120 on SpyTag and Tyr84 and Glu85 on Spycatcher play a crucial role in the formation of isopeptide bonds due to their π-π stacking effect and a salt bridge, respectively. To improve the ligation efficiency of SpyCatcher-21 ang SpyTag, a proline mutation is introduced into the E81-A91 loop of the Spycatcher-21. The introduction of Pro confers rigidity to the side chain, which in turn reduces the flexibility of E81-A91 loop and stabilizes the interactions between Tyr86 and Glu87 on SpyCatcher-21 and that between Tyr119 and Lys120 on the SpyTag. As a result, the ligation efficiencys of the SpyCatcher-21 and the SpyTag is significantly improved.

The present invention carefully considers the interaction forces among amino acids to design and modify SpyCatcher, obtaining a mutant that retains the core structure as much as possible while minimizing any significant impact on ligation efficiency. On the basis of an original molecule SpyCatcher, the SpyCatcher is subjected to negative charge modification, 10 acidic amino acid mutations are introduced on the surface of the SpyCatcher to create SpyCatcher-21, which exhibits stimulus response to pH without comprising the formation of isopeptide bond. By introducing a proline mutation at E81-A91 loop of SpyCatcher-21, the mutant SpyCatcher-21_A82P is obtained, which further improves the ligation efficiency. The SpyCatcher-21 mutant SpyCatcher-21_A82P designed by the present invention can be used to achieve double-enzyme catalysis by adjusting the pH of the environment to achieve different levels of coupling, or form a three-enzyme coupled catalytic system through electrostatic interactions with a positively charged enzyme.

BRIEF DESCRIPTION OF THE DRAWINGS

FIG. 1 shows sequence alignment of SpyCatcher-21 and SpyCatcher-21_A82P.

DETAILED DESCRIPTION

Embodiment 1

This embodiment specifically describes a design method of SpyCatcher-21_A82P.

The original SpyCatcher protein crystal structure used in this embodiment is obtained from a PDB database, and the PDB ID is 4 mli.

The structure of the SpyCatcher is imported into calculation software Rosetta to calculate the SpyCatcher, the surface potential is set to be −21, and the set mutant amino acid positions are all on the protein surface to obtain SpyCatcher-21. Then, residue 82 of the SpyCatcher-21 is introduced to Pro to obtain a SpyCatcher-21mutantSpyCatcher-21_A82P, as shown in FIG. 1.

Figure 2:
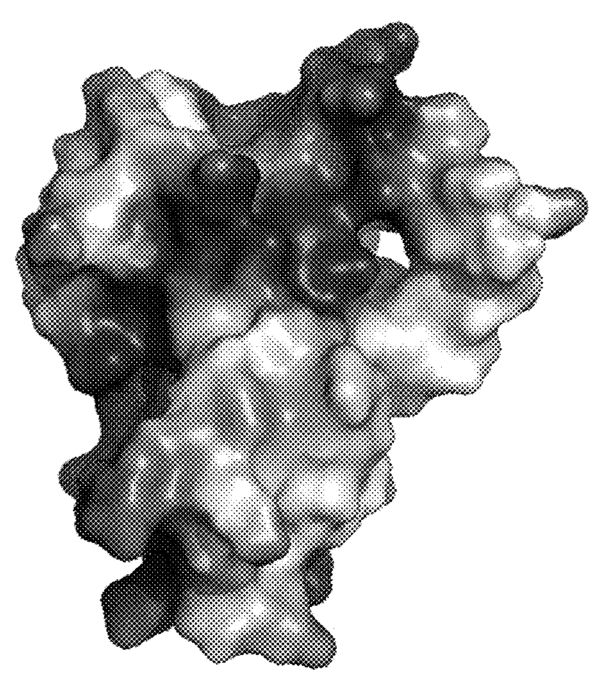
FIG. 2 is a charge density graph of SpyCatcher-21_A82P.
Figure 3:
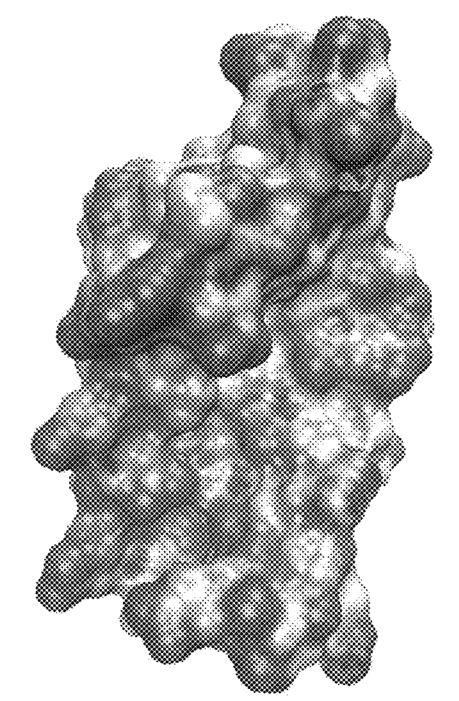
FIG. 3 is a charge density graph of SpyCatcher-21.

APBS and VMD are used to calculate the charge density of the protein surface, as shown in FIG. 2 and FIG. 3. It can be seen that the surface of the modified molecular peptide Spycatcher-21 has a large number of charges, the surface of the mutant SpyCatcher-21_A82P also has a large number of charges, and the potential is the same as that of the SpyCatcher-21.

Embodiment 2

This embodiment specifically describes a purification method of SpyCatcher-21 and SpyCatcher-21_A82P.

(1) the whole-gene synthesis of the SpyCatcher-21_A82P is obtained from Sangon Biotech (Shanghai) Co., Ltd. and cloning is conducted on a vector pET-22b to obtain a recombinant plasmid SC-21_A82P-pET-22b, wherein the restriction enzyme sites are Nde I and Xho I, and the host is *E. coli* BL21 (DE3).

(2) the *E. coli* BL21 (DE3) containing the recombinant plasmid is cultured in an LB medium at 37° C. till $OD_{600}$=0.6, and 1 M IPTG is added till a final concentration of 0.5 mM, and induction is conducted at 20° C. for 10 h.

(3) the cells are obtained after 8,000 rpm centrifugation after the end of the induction. 3 mL phosphate buffer is added and resuspended the cells, then, 300 W ultrasonication is carried out for 10 min.

(4) the supernatant is obtained after 12,000 rpm ultracentrifugation at 4° C. for 10 min, which is subsequently subjected to protein purification using Ni-NTA resin. The purified protein is dialyzed in a 3,000 Da dialysis bag for 24 h then kept for future use.

Embodiment 3

This embodiment tests the ligation efficiencies of SpyCatcher-21 at different pH values.

Mix SpyCatcher-21 and SpyTag-GFP according to a final concentration of 10 μM of SpyCatcher-21 and 30 μM of SpyTag-GFP, add buffer solutions (0.1 M) with pH=4, 5, 6, 7, 8, 9, respectively, react at 25° C. for 180 min, and measure the ligation efficiency by SDS-PAGE.

Wherein the method for purifying the protein comprises the following steps:

Drain the 20% ethanol protective liquid in the 1 mL Ni-NTA pre-packed column and add 3-4 column volumes of Buffer A to replace the ethanol in the packing. Pour the ultracentrifuged protein sample into the packing and drain it. Then add 3-4 column volumes of Buffer A for elution to remove miscellaneous protein adsorbed on the packing. Then add 3-4 column volumes of Buffer B to elute the target protein.

Buffer A is a pH 8.0 0.1 M phosphate buffer solution with 500 mM NaCl and 20 mM imidazole;

Buffer B is a pH 8.0 0.1 M phosphate buffer solution with 500 mM NaCl and 300 mM imidazole;

The 1 mL Ni-NTA pre-packed column is purchased from Sangon Biotech (Shanghai) Co., Ltd. Other reagents are all commercially available.

SDS-PAGE Protein Gel Electrophoresis Method:

Mix 30 μL of sample with 10 μL of 4× loading buffer, preserve the temperature in a 100° C. metal bath for 10 min, reduce the temperature to 4° C. after the preservation and then centrifuge at 1000-12000 rpm. Use an SDS-PAGE protein gel kit to prepare 12% separation gel and 5% concentration gel. Load 10 μL of the prepared sample, at a voltage of 120 V and an electrophoresis time of 120 min. Stain with a Coomassie brilliant blue staining solution for 60-120 min, and decolor with a destaining solution until the background is transparent. Photograph in a gel imager and perform strip density analysis by using ImageJ to obtain the ligation efficiency. The SDS-PAGE protein gel kit is purchased from Beijing Solarbio Science & Technology Co., Ltd. and other reagents are all commercially available.

Figure 4:
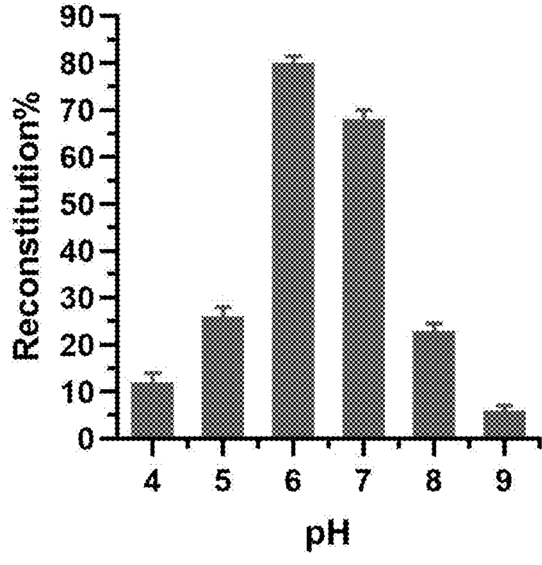
FIG. 4 shows the ligation efficiencies under different pH environments.
Figure 5:
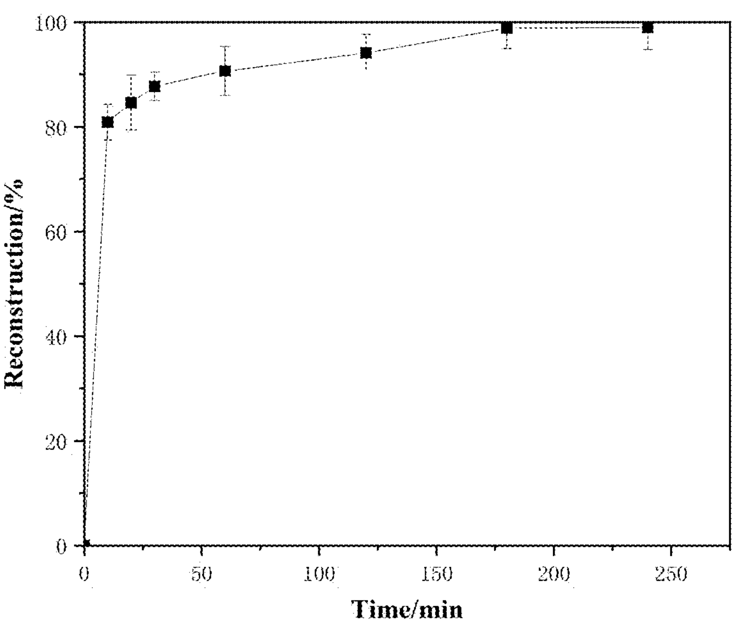
FIG. 5 shows the dynamics of SpyCatcher-21_A82P.
Figure 6:
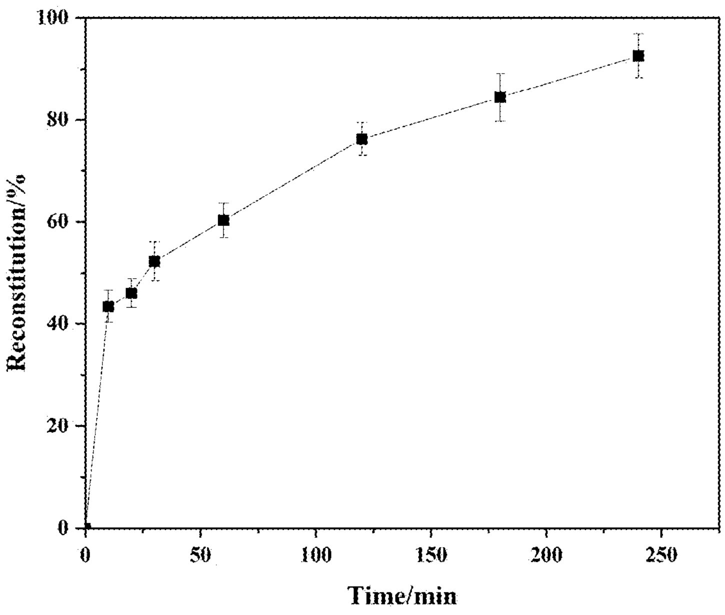
FIG. 6 shows the dynamics of SpyCatcher-21.

The results are as shown in FIG. 4, SpyCatcher-21 has the ability to form an isopeptide bond with SpyTag, has a large number of negative charges on the surface and can also have stimulus response to pH. SpyCatcher-21_A82P also has response to pH.

Embodiment 4

This embodiment compares the ligation efficiencies of SpyCatcher-21 and SpyCatcher-21_A82P when the pH value is 6.

Mix SpyCatcher-21_A82P and SpyTag-GFP according to a final concentration of 10 μM of SpyCatcher-21_A82P and 30 μM of SpyTag-GFP, measure the ligation efficiencies of SpyCatcher-21_A82P and SpyTag-GFP at 25° C. and 0, 10, 20, 30, 40, 50, 60, 120, 180, 240 min, respectively, and measure the ligation efficiency by SDS-PAGE.

The results indicate that the ligation rate of SpyCatcher-21 is ~42% at 10 min, and ~90% at 240 min. The modified SpyCatcher-21_A82P can reach a ligation efficiency of ~80% at 10 min and 100% at 180 min, and SpyCatcher-21_A82P significantly improves the ligation efficiency while maintaining potential and pH response.

The invention claimed is:

1. A molecular peptide mutant obtained from *Streptococcus pyogenes*, wherein the peptide has the amino acid sequence set forth in SEQ ID NO: 1 and wherein the peptide forms isopeptide bonds.

* * * * *